United States Patent [19]

Ternström et al.

[11] Patent Number: 5,037,417
[45] Date of Patent: Aug. 6, 1991

[54] SANITARY NAPKIN

[75] Inventors: Maj I. Ternström, Mölnlycke; Roy Hansson, Mölndal, both of Sweden

[73] Assignee: Molnlycke AB, Gothenburg, Sweden

[21] Appl. No.: 368,399

[22] PCT Filed: Dec. 17, 1987

[86] PCT No.: PCT/SE87/00611
§ 371 Date: Jun. 2, 1989
§ 102(e) Date: Jun. 2, 1989

[87] PCT Pub. No.: WO88/04546
PCT Pub. Date: Jun. 30, 1988

[30] Foreign Application Priority Data

Dec. 23, 1986 [SE] Sweden ............................ 8605550

[51] Int. Cl.⁵ ............................................. A61F 13/15
[52] U.S. Cl. .............................. 609/385.2; 609/387; 609/389
[58] Field of Search ................ 206/438, 439, 440; 609/385.1, 385.2, 386, 387, 389, 390, 393, 397, 400, 401, 402

[56] References Cited

U.S. PATENT DOCUMENTS

| | | | |
|---|---|---|---|
| 3,970,087 | 7/1976 | Castaneda | 604/387 |
| 3,973,567 | 8/1976 | Srinivasan et al. | 604/387 |
| 4,285,343 | 8/1981 | McNair | |
| 4,589,876 | 5/1986 | Van Tilburg | 604/393 |
| 4,608,047 | 8/1986 | Mattingly | 604/387 |
| 4,692,163 | 9/1987 | Widlund et al. | 604/385.2 |
| 4,735,316 | 4/1988 | Fröidh et al. | 604/397 |
| 4,846,828 | 7/1989 | Mendelsohn | 604/387 |
| 4,857,066 | 8/1989 | Allison | 604/387 |
| 4,897,084 | 1/1990 | Ternstöm et al. | 604/388.2 |
| 4,911,701 | 3/1990 | Mavinkurve | 604/385.2 |

FOREIGN PATENT DOCUMENTS

| | | | |
|---|---|---|---|
| 0127103 | 12/1984 | European Pat. Off. | |
| 0130848 | 1/1985 | European Pat. Off. | |
| 0134086 | 3/1985 | European Pat. Off. | |
| 0231974 | 8/1987 | European Pat. Off. | 604/388 |
| 2143439 | 2/1985 | United Kingdom | |

Primary Examiner—David J. Isabella
Assistant Examiner—K. M. Reichl
Attorney, Agent, or Firm—Young & Thompson

[57] ABSTRACT

A sanitary napkin for placement in the crotch portion of a panty, which comprises an elongated absorbent body with a front end and a rear end and opposite longitudinal edges extending lengthwise of the absorbent body from the front end to the rear end. The absorbent body is enclosed in a casing having flaps extending laterally from each of the longitudinal edges of the absorbent body along at least the front end thereof, each flap having a front edge and having such an extent that an outer part thereof is foldable around a lateral edge of the front part of a panty. Adhesive layers are provided on the outer parts close to the front edges and spaced a substantial distance from the longitudinal edges, whereby the position of the sanitary napkin in a panty can be readjusted, when the panty is on the wearer, with the aid of the outer parts of the flaps. The side flaps taper from the front end of the absorbent body so as to converge toward the rear end of the absorbent body. There can also be an adhesive layer on the side of the rear end of the casing that faces the panty during use.

6 Claims, 2 Drawing Sheets

SANITARY NAPKIN

FIELD OF THE INVENTION

The present invention relates to a sanitary napkin consisting of an absorbent body and a casing surrounding it.

BACKGROUND OF THE INVENTION

Leakage arising from sanitary napkins or pantiliners are in most cases caused by improper positioning of the napkin already on its application in a panty, or by the absorbent body being at least partially displaced from its initial position.

Sanitary napkins having flaps projecting laterally from the center of the absorbent body, which primarily serve to protect the crotch portion of the panty from discoloration, are previously known. Although preventing to a certain degree lateral displacement of the sanitary napkin in the crotch portion, such flaps do not support the absorbent body at its ends.

OBJECT OF THE INVENTION

The object of the invention is to improve a napkin of this type so as to reduce the risk of leakage associated with sanitary napkins.

BRIEF SUMMARY OF THE INVENTION

This object is achieved with a sanitary napkin according to the invention. By the flaps being located at the front edge of the napkin they will be more readily accessible, enabling them in this manner to be secured to the outside of the panty after putting it on. Also, the inventive napkin is more easily fitted into its proper position since adjustment can be done at the end instead of at the center of the napkin.

In a preferred embodiment of the invention, the side flaps extend in the longitudinal direction of the absorbent body from the end of the napkin intended to be placed in front, and up to at least the center of the absorbent body. Furthermore, the side flaps are made tapering from said front end of the napkin.

The inventive design of the flaps will enable the napkin to be folded into packages prior to as well as subsequent to usage, which is a great advantage from the user's aspect.

BRIEF DESCRIPTION OF THE DRAWINGS

These and other features and advantages will be disclosed in more detail in the following description of an embodiment of the inventive sanitary napkin with reference to the accompanying drawings, of which

DETAILED DESCRIPTION OF THE INVENTION

The sanitary napkin illustrated by the figures comprises an absorbent body 1 encapsulated in a casing which is composed of two interconnected surface layers 2, 3. The surface layer 2, which is a liquid impermeable layer facing the panty during use of the napkin and therefore constitutes the so-called outside of the casing, is secured at spaced points to the panty as will be explained later on, whereas the surface layer 3 is a liquid permeable layer facing the wearer's body during use and constituting therefor the so-called inside of the casing.

Figure 1:
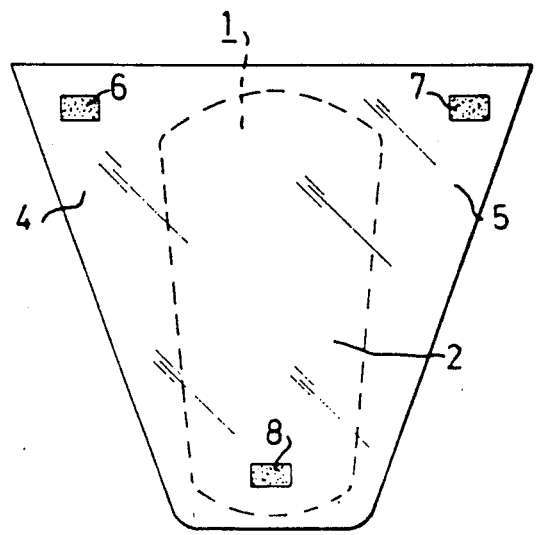
FIG. 1 shows a sanitary napkin according to the invention with the side intended for attachment inside a panty facing the viewer.

As can be seen from the figures, at least one end of the casing has lateral extensions forming side flaps 4, 5. In FIG. 1 the side flaps extend from one end of the napkin to the other end thereof and are made tapering from the upper end as seen in the figure, which end is to be forwardly placed within a panty for which reason it is referred to in the following as the front end of the napkin. The casing is provided on its outside with adhesive layers 6, 7 located at the forward ends of the side flaps, as well as an adhesive layer 8 disposed at the rearward end on the outside of the casing, said adhesive layers serving as attachment means for the napkin inside the panty.

Application of the sanitary napkin takes place in the following manner. The napkin is placed inside a partially pulled down panty which is then pulled up. If the napkin is properly positioned, which is easily ascertained when the panty is put on, the laterally projecting flaps 4, 5 are folded around the edge of the panty and the adhesive layers 6, 7 are affixed to the outside of the panty. In case of backward or sideward misplacement of the napkin, readjustment can be accomplished with the aid of the side flaps which are accessible from without. If however the napkin is initially placed too far up front in the panty and has to be pulled backwards, the panty must be loosened to permit such rearrangement.

It should be understood that after some time the wearer will learn to avoid placement of the napkin so that the front end has to be moved downwards, and therefore readjustments requiring loosening of the panty will be rarely occurring incidents. The inventive napkin is thus simpler to fit into position than prior art sanitary napkins.

There is no need to provide the rear end of the napkin with any adhesive layer. In many cases a friction liner could suffice as a safeguard against displacement of the rear end of the napkin in relation to the panty. Moreover, by replacing the rear adhesive layer of the napkin with a friction liner, readjustment of the napkin in the panty is facilitated.

In order to further stabilize the position of the napkin in the panty, elastic members such as elastic threads, for example, may be disposed longitudinally along the side edges of the flaps which would reduce to a high degree the risk of the absorbent body moving sidewards relative to the panty and away from its initial position. To achieve this performance, the rear end of the napkin should be provided with an adhesive layer 8 serving to prevent the napkin from contraction caused by the force of the elastic members.

Figure 2:
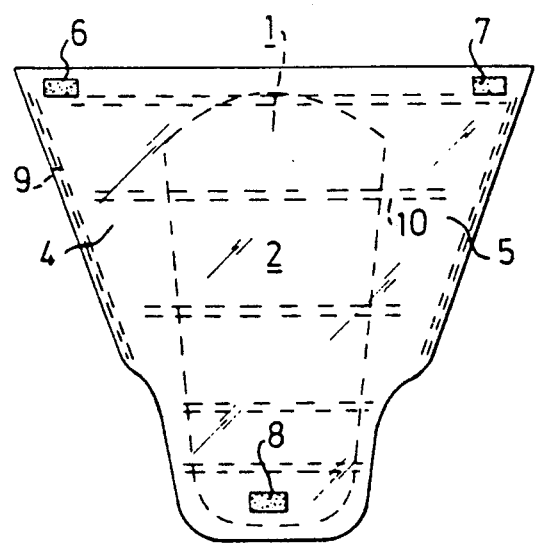
FIG. 2 shows an alternative embodiment of the sanitary napkin according to FIG. 1.
Figure 3A:
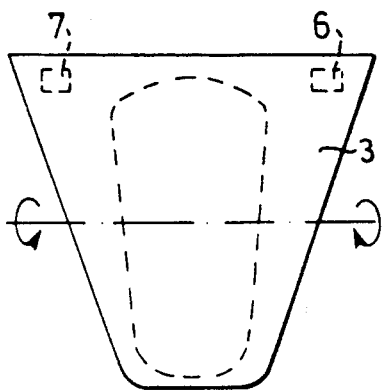
FIGS. 3a-3d show the various steps of folding the sanitary napkin according to Claim 1 into a package.
Figure 3B:
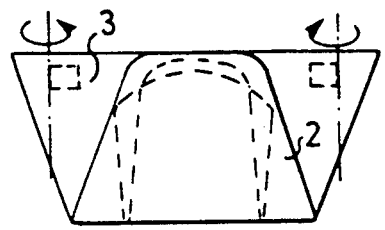
Figure 3C:
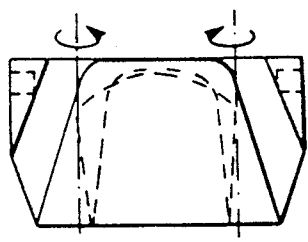
Figure 3D:
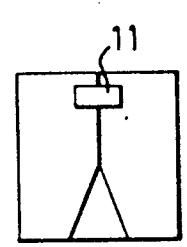

According to FIG. 2, wherein like reference numerals refer to the same elements as in FIG. 1, the sanitary napkin differs from the one shown in FIG. 1 in that the side flaps 4, 5 have a shorter extension in their longitudinal direction, creating in this manner folding indications, and in that the napkin of FIG. 2 also includes longitudinal and transverse elastic members 9, 10. The transverse elastic members 10 are intended to give the absorbent body a tendency of curving inwards for preventing gap formation between napkin and outer genitals should the panty with its associated napkin be somewhat displaced in relation thereto such as, for example, by squirming in a cinema chair. In other words, the napkin may so to say be spring loaded towards an inwardly bent shape. The transverse elastic members 10 are for this purpose arranged in the surface layer 2 and preferably on the side thereof facing the absorbent body 1.

It has been found advantageous to design a napkin acording to FIG. 1 with only one transverse thread in the proximity of the upper edge of the napkin.

Due to the inventive design including side flaps, the napkin can be folded to form its own hygienic package. The advantage gained is that single, unused napkins can be hygienically brought along in a handbag, for example, enabling simultaniously a used napkin to be folded into a hygienic and discretely disposable item.

FIG. 3 illustrates the method of folding a used napkin according to FIG. 1 into the form of a package. Folding axes are indicated by dash-dotted lines, and folding directions with arrows in the figure. The napkin according to FIG. 1 is thus folded about its center so that the rear end is bent in over the front end to lie flush therewith, the folding direction being such taht the liquid impermeable surface layer 2 is turned outwards (see FIG. 3a). Next, the portions of the side flaps lying beyond the adhesive layers 6, 7 are folded in over the inside of the casing along folding lines extending parallel with the longitudinal direction of an unfolded napkin (see FIG. 3b). Finally, the free casing portions are folded in over the absorbent body along folding axes extending parallel with the longitudinal direction of an unfolded napkin so that the casing edges folded over to lie flush with the outer limit of the adhesive layers will come close together without leaving any gap between the adhesive layers 6 and 7 (FIG. 3c). The napkin thus folded into a package is then sealed with the aid of a foil strip 11 treated with release agent and covering the juxtaposed adhesive layers 6, 7 (FIG. 3d).

The folding process described above may in principle be applied also in connection with packing unused napkins. In order to minimize the requirement of space, these napkins should however be folded into three sections before folding in the flaps.

It should be emphasized in this context that in the manufacture of the inventive napkin, the adhesive layers 6, 7 could suitably be applied after the napkin has reached its finally folded state. The folding procedure could be further simplified by giving the flaps some other configuration, for example by cutting off the triangular flap portions situated beyond the adhesive layers and which are located in FIG. 3b beyond the folding axes.

The methods of folding described above are only given as non-limiting illustrative examples on how to fold a napkin having flaps according the FIG. 1 into a package. Other folding processes could be utilized for example when folding napkins with alternatively shaped flaps.

According to the present invention there is thus achieved a sanitary napkin which is easily fixed in its proper position inside the panty and which permits adjustment of the napkin after the panty is put on. Furthermore, the napkin is held firmly and securely fixed in the panty during use, and finally the side flaps will permit the napkin to be folded into a hygienic single-piece package prior to as well as subsequent to use, the invention thereby eliminating to a high degree the problem of bringing along and disposing of separate napkins.

A plurality of modifications are of course conceivable within the scope of the inventive idea, particularly with regard to the shape of the absorbent body and the casing flaps. The invention should therefore be restricted solely by the contents of the following patent claims.

We claim:

1. A sanitay napkin for placement in the crotch portion of a panty, which napkin comprises an elongated absorbent body with a front end and a rear end and opposite longitudinal edges extending lengthwise of said absorbent body from said front end to said rear end, said body being enclosed in a casing having flap means extending laterally from each of the longitudinal edges of the absorbent body along at least the front end thereof, each flap means having a front edge and having such an extent that the lateral outer part thereof is for folding around a lateral edge of the front part of the crotch portion of the panty, and adhesive means on the said outer parts close to said front edges yet spaced a substantial distance from said longitudinal edges, whereby the position of the sanitary napkin in a panty can be readjusted, when the panty is on the wearer, with the aid of said outer parts of the flap means 2. A sanitary napkin according to claim 1, wherein the flap means taper from said front end of the absorbent body so as to converge toward said rear end of the absorbent body.

3. A sanitary napkin according to claim 1, there also being adhesive means on the rear end of the casing for facing the panty during use.

4. A sanitary napkin according to claim 1, wherein said flap means include lateral edges and elastic members disposed along said lateral edges of the flap means.

5. A sanitary napkin according to claim 1, the casing being composed of two surface layers, and transverse elastic members disposed in the surface layer of the casing adapted to face the panty in use.

6. A sanitary napkin according to claim 1, wherein the body is folded over itself transverse to said longitudinal edges and the flap means are bent in over the folded body and lie edge to edge with said adhesive means adjoining each other, and a single protective foil strip extending over the adjoining adhesive means and holding the napkin folded.

* * * * *